US009232992B2

(12) United States Patent
Heidner et al.

(10) Patent No.: US 9,232,992 B2
(45) Date of Patent: Jan. 12, 2016

(54) MULTI-LAYERED MEDICAL DEVICE FOR TREATING A TARGET SITE AND ASSOCIATED METHOD

(75) Inventors: Matthew C. Heidner, Maple Grove, MN (US); Daniel O. Adams, Long Lake, MN (US)

(73) Assignee: AGA MEDICAL CORPORATION, Plymouth, MN (US)

( * ) Notice: Subject to any disclaimer, the term of this patent is extended or adjusted under 35 U.S.C. 154(b) by 573 days.

(21) Appl. No.: 12/179,157

(22) Filed: Jul. 24, 2008

(65) Prior Publication Data

US 2010/0023046 A1 Jan. 28, 2010

(51) Int. Cl.
*A61F 2/06* (2013.01)
*A61B 17/12* (2006.01)
*A61F 2/24* (2006.01)
*A61B 17/00* (2006.01)
*A61F 2/07* (2013.01)

(52) U.S. Cl.
CPC .............. *A61F 2/06* (2013.01); *A61B 17/12036* (2013.01); *A61B 17/12109* (2013.01); *A61B 17/12118* (2013.01); *A61B 17/12172* (2013.01); *A61B 17/12177* (2013.01); *A61F 2/2493* (2013.01); *A61B 2017/00526* (2013.01); *A61B 2017/00592* (2013.01); *A61B 2017/00606* (2013.01); *A61B 2017/00623* (2013.01); *A61B 2017/00867* (2013.01); *A61F 2/07* (2013.01); *A61F 2002/068* (2013.01)

(58) Field of Classification Search
CPC ................... A61B 17/12036; A61B 17/12118; A61B 17/12177; A61B 17/12109; A61B 17/12172; A61B 2017/00526; A61B 2017/00606; A61B 2017/00867; A61B 2017/00592; A61B 2017/00623; A61F 2/2493; A61F 2/06; A61F 2/07
USPC ......... 606/200, 213, 191, 194; 623/1.11, 1.13, 623/1.15, 1.2
See application file for complete search history.

(56) References Cited

U.S. PATENT DOCUMENTS 5,522,881 A * 6/1996 Lentz ........................... 623/1.13
5,709,713 A 1/1998 Evans et al.
(Continued)

FOREIGN PATENT DOCUMENTS

WO WO 98/52476 A1 11/1998
WO WO-2006/128185 A2 11/2006
WO WO 2008/025405 A1 3/2008

OTHER PUBLICATIONS

Related U.S. Appl. No. 11/966,397, entitled "Percutaneous Catheter Directed Intravascular Occlusion Devices," filed Dec. 28, 2007.
(Continued)

*Primary Examiner* — Jing Ou
(74) *Attorney, Agent, or Firm* — Armstrong Teasdale LLP

(57) ABSTRACT

Embodiments of the present invention provide medical devices and methods for treating a target site within the body, such as for treating vascular abnormalities. For example, one embodiment provides a stent graft including an occlusive material having a preset, overlapping configuration comprising at least three inverted overlapping layers that are folded over one another. The at least three inverted overlapping layers are configured to be separated and disposed within a catheter in a non-overlapping configuration and return to the preset, overlapping configuration when deployed from the catheter.

22 Claims, 5 Drawing Sheets

(56) References Cited

U.S. PATENT DOCUMENTS

| | | | |
|---|---|---|---|
| 5,725,552 A | 3/1998 | Kotula et al. | |
| 5,733,294 A | 3/1998 | Forber et al. | |
| 5,755,772 A * | 5/1998 | Evans et al. | 128/898 |
| 5,846,261 A * | 12/1998 | Kotula et al. | 606/213 |
| 5,944,738 A | 8/1999 | Amplatz et al. | |
| 6,123,715 A | 9/2000 | Amplatz | |
| 6,287,335 B1 * | 9/2001 | Drasler et al. | 623/1.28 |
| 6,368,339 B1 | 4/2002 | Amplatz | |
| 6,447,531 B1 | 9/2002 | Amplatz | |
| 6,506,204 B2 | 1/2003 | Mazzocchi | |
| 6,579,303 B2 | 6/2003 | Amplatz | |
| 6,599,308 B2 | 7/2003 | Amplatz | |
| 6,797,083 B2 | 9/2004 | Peterson | |
| 6,866,679 B2 | 3/2005 | Kusleika | |
| 7,060,089 B2 * | 6/2006 | Ley et al. | 623/1.15 |
| 2003/0040771 A1 * | 2/2003 | Hyodoh et al. | 606/200 |
| 2004/0210244 A1 | 10/2004 | Vargas et al. | |
| 2005/0137702 A1 * | 6/2005 | Haug et al. | 623/2.38 |
| 2005/0155612 A1 | 7/2005 | Matsuura et al. | |
| 2006/0009799 A1 | 1/2006 | Kleshinski et al. | |
| 2006/0116716 A1 | 6/2006 | Gerberding | |
| 2006/0247680 A1 | 11/2006 | Amplatz et al. | |
| 2006/0253181 A1 | 11/2006 | Schulman et al. | |
| 2006/0271166 A1 * | 11/2006 | Thill et al. | 623/1.23 |
| 2007/0118207 A1 | 5/2007 | Amplatz et al. | |
| 2007/0265656 A1 | 11/2007 | Amplatz et al. | |
| 2008/0071356 A1 * | 3/2008 | Greenhalgh et al. | 623/1.16 |
| 2008/0132996 A1 | 6/2008 | Drasler et al. | |
| 2009/0210047 A1 | 8/2009 | Amplatz et al. | |
| 2010/0023048 A1 | 1/2010 | Mach | |

OTHER PUBLICATIONS

Related U.S. Appl. No. 11/827,590, entitled "Percutaneous Catheter Directed Intravascular Occlusion Devices," filed Jul. 12, 2007.

Chinese Office Action for Application No. 200980128923.2, dated Apr. 3, 2013.

Japanese Office Action for Application No. 2011-520064, dated May 15, 2013.

* cited by examiner

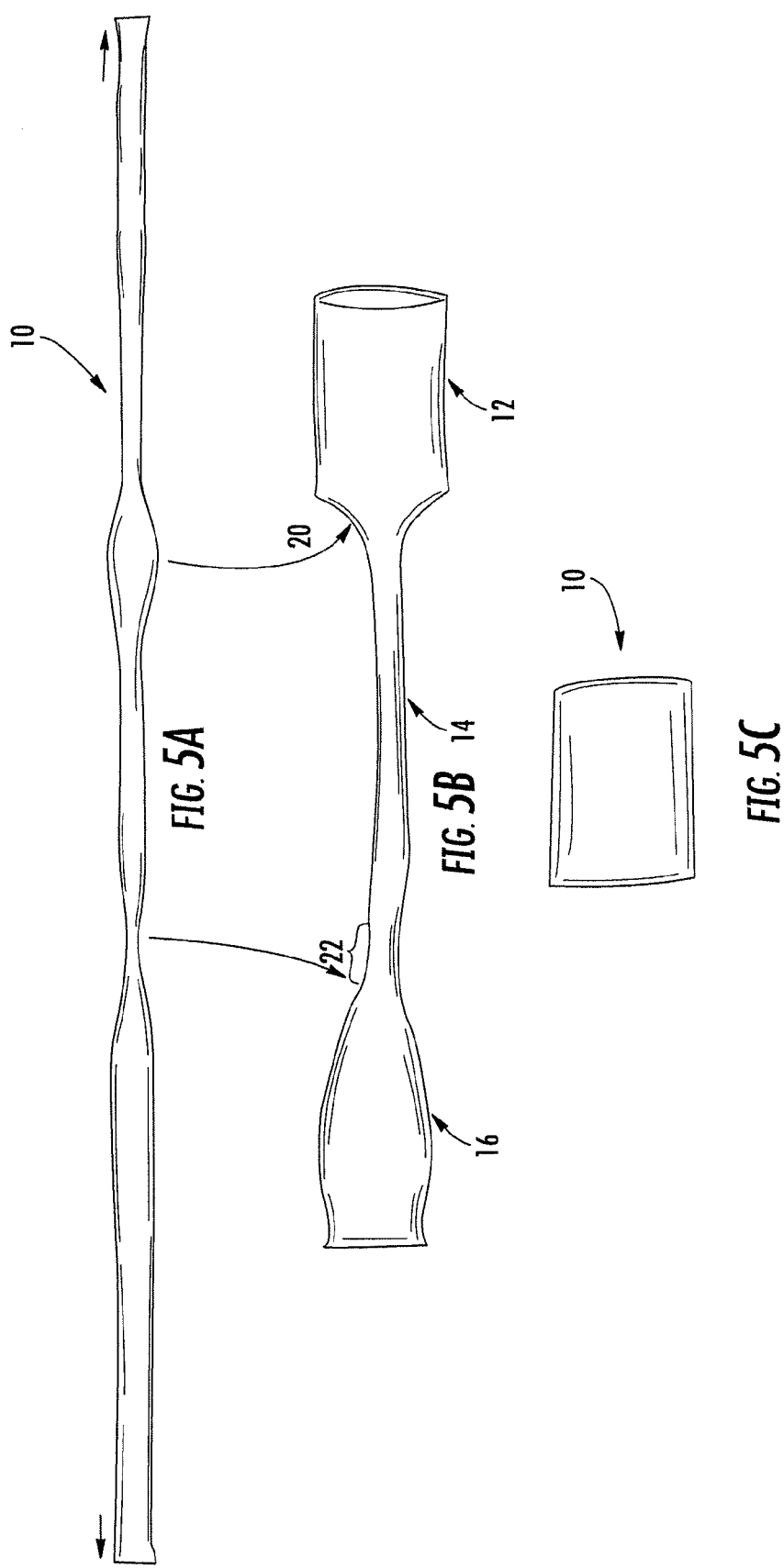

MULTI-LAYERED MEDICAL DEVICE FOR TREATING A TARGET SITE AND ASSOCIATED METHOD

BACKGROUND OF THE INVENTION

1) Field of the Invention

The present invention relates to medical devices and, in particular, to a multi-layered device for treating a target site within the body, such as a vascular abnormality.

2) Description of Related Art

Medical devices such as occluders, flow restrictors, shunts, and stent/grafts are known in the art. For example, devices may be made with a single layer of braided wire fabric to occlude, restrict, or shunt flow through vessels, organs, cavities, or the like. These single-layered devices may be elongated to a reduced diameter for delivery through a catheter and resume their memorized shape when released from the delivery catheter.

Medical devices, such as multi-layered occluders and stent grafts, have also been developed in order to occlude or exclude vascular abnormalities. For example, the medical devices may include multiple layers of coaxially disposed layers of material that are configured to substantially slow the flow of blood and facilitate thrombosis. The idea is that having a greater metallic surface area using a multi-layered device speeds clot formation in comparison to single layer devices and eliminates the need for an additional material such as a polyester fabric often included in single layer devices. If the layers of material are tied together, the layers must elongate the same to be able to be tied at the middle of their longitudinal axis and to be grasped at their ends for loading within a delivery system. If the layers do not elongate the same, one of the layers will be longer than the others in a drawn down configuration, such that some of the layers will be difficult to grasp for delivery. When the layers have the same elongation, the braid geometry is similar between the layers, which can create holes in the device when the layers line up the same. Altering the braid geometry may prevent these gaps, but may lead to differences in elongation, as described above.

Multi-layer devices may be lower in delivery profile than single metal layer devices which incorporate an additional polyester fabric to facilitate occlusion because the metal filaments in a multi-layer device use smaller diameter wire and the multiple layers can all be reduced substantially in diameter together by elongation, where as the polyester fabric must be folded over itself for delivery, causing greater delivery profile in single layer devices. The profile for delivery of multiple layer devices is determined by the additive thickness of each layer in the elongated state. It would be advantageous, if all the benefits of a multi-layer device could be achieved with a lower delivery profile such as by delivering each layer sequentially. A lower delivery profile would provide for a smaller sized delivery catheter, a smaller puncture size into the vasculature, and less trauma to the vascular tissue in passage of the delivery catheter through the vasculature. In addition, smaller catheters are more flexible, and the device may be able to be placed in more difficult to reach anatomical sites such as through smaller diameter vessels or through more tortuous pathways.

Therefore, there is a need for a medical device that is capable of effectively treating various target sites within the body. Moreover, there is a need for a medical device that may be easily delivered and adequately anchored at the target site. In addition, there is a need for a medical device that may be delivered to a target site that is less traumatic to the vasculature and that may be used to prophylactically treat various conditions that may be in more difficult to reach anatomy.

BRIEF SUMMARY OF THE INVENTION

Embodiments of the present invention may provide improvements over the prior art by, among other things, providing medical devices and methods for treating a target site within the body. For example, the medical device may be a stent graft, a shunt, or a flow restrictor device for treating various target sites. According to one embodiment of the present invention, a medical device for treating a target site is provided and includes an occlusive material having a preset, overlapping configuration comprising at least three inverted overlapping layers that are folded over one another. The at least three inverted overlapping layers are configured to be separated and disposed within a catheter in a non-overlapping configuration and return to the preset, overlapping configuration when deployed from the catheter. Moreover, the occlusive material is configured to provide a central passageway for fluid flow therethrough in the preset, overlapping configuration.

According to various aspects of the medical device, the occlusive material is a continuous layer of fabric, such as a fabric braided of strands of an elastic metal alloy (e.g., Nitinol). The occlusive material may be configured to be axially elongated to separate the at least three inverted overlapping layers into the non-overlapping configuration. The occlusive material may include an overlapping configuration having a tubular shape, wherein at least one of the at least three inverted overlapping layers is configured to fold within another layer in an axial direction. Each layer may be about the same length. The occlusive material is configured to be constrained to an outer diameter of less than about 11 French for delivery within a catheter in the non-overlapping configuration. The overlapping configuration may have a larger outer diameter and shorter length than the non-overlapping configuration.

The occlusive material may include an inner surface and an outer surface, and at least a portion of the occlusive material may be configured to fold within itself such that a portion of the inner surface overlies another portion of the inner surface. At least a portion of the occlusive material may be configured to fold within itself such that a portion of the outer surface overlies a portion of the inner surface. Furthermore, at least a portion of at least one of the at least three inverted overlapping layers may be configured to fold within and lie adjacent to another layer. At least one pair of the at least three inverted overlapping layers may be configured to fold greater than about 180 degrees with respect to one another. At least a pair of non-adjacent inverted overlapping layers may include surface portions that are configured to lie substantially parallel to one another in the overlapping configuration. At least one pair of the at least three inverted overlapping layers may be configured to fold about 180 degrees or less with respect to one another.

An additional embodiment of the present invention provides a method for delivering a medical device to a target site wherein the medical device may be a stent graft, flow restrictor, or shunt. The method includes axially elongating a medical device having a preset, overlapping configuration such that at least three inverted overlapping layers are separated into a non-overlapping configuration. The method further includes positioning the medical device in the non-overlapping configuration into the lumen of a catheter, delivering the medical device proximate to the target site, and deploying the medical device from the catheter lumen such that the medical device returns to the overlapping configuration and provides a central passageway for fluid flow therethrough in the preset, overlapping configuration.

According to aspects of the method, the deploying step includes retracting the catheter to at least partially release the medical device. The deploying step may include urging the proximal end of the medical device distally to invert a first portion of the medical device within a second portion of the medical device to form two layers of the overlapping configuration. The deploying step may include deploying the medical device such that at least a pair of the at least three inverted overlapping layers are folded at least about 180 degrees with respect to one another. The deploying step may include deploying the medical device such that the medical device is configured to self-expand and return to the overlapping configuration when deployed from the catheter. The axially elongating step may include axially elongating the medical device to an outer diameter of less than about 11 French. Furthermore, the axially elongating step may include axially elongating the medical device into the non-overlapping configuration having a substantially smaller diameter and a substantially greater length than the overlapping configuration. The delivering step may include delivering the medical device over a guide wire.

Another embodiment provides a method of fabricating a medical device. The method includes providing an occlusive material braided into a tubular member having an initial length and manipulating the tubular member to define an overlapping configuration having at least three inverted overlapping layers and a length less than the initial length. The method also includes positioning the occlusive material on a mandrel and/or within a mold and heat setting the occlusive material in the overlapping configuration such that the at least three, or a plurality of, inverted overlapping layers are configured to be separated by elongation of the opposed ends and disposed within a delivery catheter in a non-overlapping configuration and to return to the preset, overlapping configuration when deployed from the delivery catheter. The medical device is also heat set such that the occlusive material is configured to provide a central passageway for fluid flow therethrough in the preset, overlapping configuration.

According to an additional aspect of the present invention, a medical device (e.g., a stent graft or flow restrictor) is provided that includes an occlusive material having a preset, overlapping configuration having a plurality of inverted overlapping layers. The plurality of inverted overlapping layers are folded at least about 180 degrees with respect to one another. The plurality of inverted overlapping layers are configured to be separated and disposed within a catheter in a non-overlapping configuration and return to the preset, overlapping configuration when deployed from the catheter. At least a pair of non-adjacent inverted overlapping layers may include surface portions that are configured to be substantially parallel to one another in the overlapping configuration.

BRIEF DESCRIPTION OF THE SEVERAL VIEWS OF THE DRAWINGS

Figure 6A:
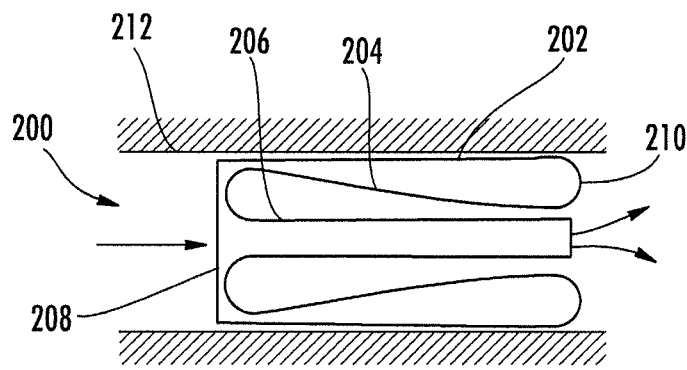
Figure 6B:
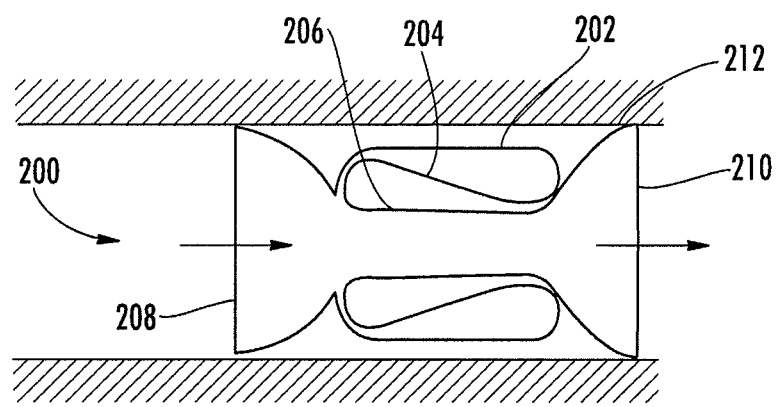
Figure 6C:
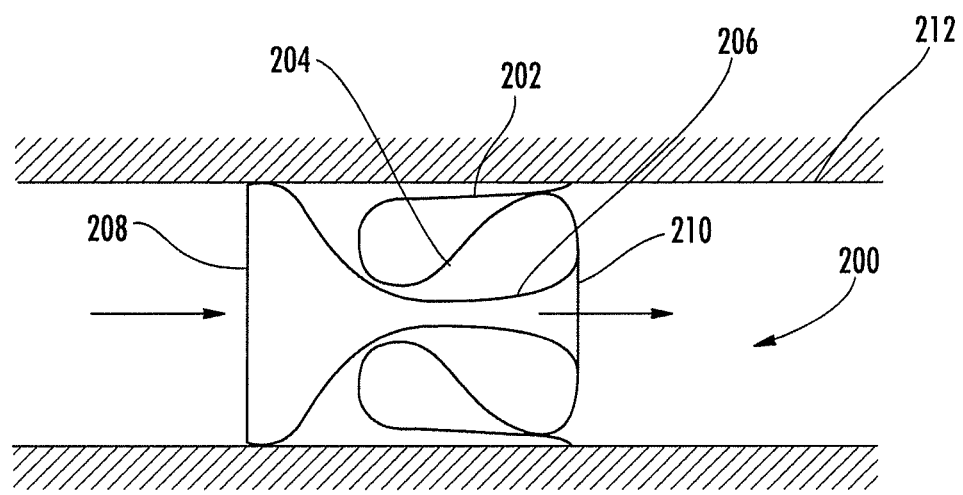
Figure 7:
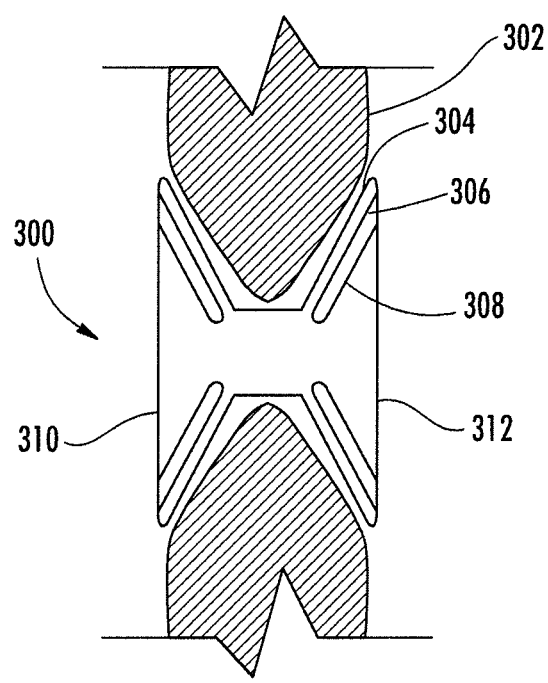

Having thus described the invention in general terms, reference will now be made to the accompanying drawings, which are not necessarily drawn to scale, and wherein:

FIGS. 1-4 illustrate cross-sectional views of multi-layered grafts according to various embodiments of the present invention;

FIG. 5A-C depict a side elevational view of a multi-layered graft in an elongated configuration (A), a non-overlapping relaxed configuration (B), and an overlapping relaxed configuration (C), according to one embodiment of the present invention;

FIGS. 6A-C illustrate cross-sectional views of flow restrictors or shunts according to additional embodiments of the present invention; and FIG. 7 depicts a cross-sectional view of a shunt according to one embodiment of the present invention.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Embodiments of the present invention provide a medical device for use in treating a target site within the body, such as a stent graft for excluding various vascular abnormalities, which may include, for example, excluding an aneurysm. The device may also be used as a flow restrictor or a shunt, filter or other type of device for placement in the vascular system, as well as a graft for lining a lumen of a vessel. It is understood that the use of the term "target site" is not meant to be limiting, as the device may be configured to treat any target site, such as an abnormality, a vessel, an organ, an opening, a chamber, a channel, a hole, a cavity, or the like, located anywhere in the body. For example, the abnormality could be any abnormality that affects the shape or the function of the native lumen, such as an aneurysm, a lesion, a vessel dissection, flow abnormality or a tumor. Furthermore, the term "lumen" is also not meant to be limiting, as the abnormality may reside in a variety of locations within the vasculature, such as a vessel, an artery, a vein, a passageway, an organ, a cavity, or the like.

As explained in further detail below, a medical device according to one embodiment of the present invention includes an overlapping configuration including a plurality of overlapping layers of occlusive material. The plurality of layers are configured to be separated into a non-overlapping configuration for delivery within a catheter and return to the overlapping configuration when deployed from the catheter. In the preset, overlapping configuration, the occlusive material may be configured to provide a central passageway or lumen for fluid flow therethrough (e.g., blood flow through a stent graft).

According to one embodiment of the present invention for forming a medical device of the invention, the device includes a braided fabric formed of a plurality of wire strands having a predetermined relative orientation with respect to one another. Moreover, the device may comprise a plurality of layers of occlusive material such that the device may be a variety of occluding materials capable of at least partially inhibiting blood flow therethrough in order to facilitate the formation of thrombus and epithelialization around the device.

Although the term "strand" is discussed herein, "strand" is not meant to be limiting, as it is understood the fabric may comprise one or more wires, cords, fibers, yarns, filaments, cables, threads, or the like, such that such terms may be used interchangeably.

As used herein, "substantially preclude or impede flow" shall mean, functionally, that blood flow may occur for a short time, e.g., about 3-60 minutes through the occlusive material, but that the body's clotting mechanism or protein or other body deposits on the braided wire strands results in occlusion or flow stoppage after this initial time period. For instance, occlusion may be clinically represented by injecting a contrast media into the upstream lumen of the device and if no contrast media flows through the wall of the device after a predetermined period of time as viewed by fluoroscopy, then the position and occlusion of the device is adequate. Moreover, occlusion of the target site could be assessed using various ultrasound echo doppler modalities.

As used herein the term "proximal" shall mean closest to the operator (less into the body) and "distal" shall mean furthest from the operator (further into the body). In positioning of the medical device from a downstream access point, distal is more upstream and proximal is more downstream.

According to one embodiment, the occlusive material is a metal fabric including a plurality of strands, such as two sets of essentially parallel generally helical strands, with the strands of one set having a "hand", i.e., a direction of rotation, opposite that of the other set. The strands may be braided, interwoven, or otherwise combined to define a generally tubular fabric.

The pitch of the strands (i.e., the angle defined between the turns of the strands and the axis of the braid) and the pick of the fabric (i.e., the number of wire strand crossovers per unit length) may be adjusted as desired for a particular application. The wire strands of the metal fabric used in one embodiment of the present method may be formed of a material that is both resilient and can be heat treated to substantially set a desired shape. One factor in choosing a suitable material for the wire strands is that the wires retain a suitable amount of the deformation induced by the molding surface (as described below) when subjected to a predetermined heat treatment and elastically return to said molded shape after substantial deformation.

One class of materials which meets these qualifications is so-called shape memory alloys. One particularly preferred shape memory alloy for use in the present method is Nitinol. NiTi alloys are also very elastic—they are said to be "superelastic" or "pseudoelastic". This elasticity may allow the device to return to a preset expanded configuration for deployment following passage in a distorted form through a delivery catheter. It is also understood that the device may comprise various materials other than Nitinol that have elastic properties, such as spring stainless steel, trade named alloys such as Elgiloy, Hastalloy, Phynox, MP35N, or CoCrMo alloys. Depending on the individual material selected, the wire strand diameter, number of wire strands and pitch may be altered to achieve the desired properties of the device. Moreover, other suitable materials include those that are compatible with magnetic resonance imaging (MRI), as some materials may cause heat or torque resulting from performing MRI, and some materials may distort the MRI image. Thus, metallic and/or non-metallic materials that reduce or eliminate these potential problems resulting from using MRI may be employed.

In forming a medical device according to one embodiment of the present invention, an appropriately sized piece of the fabric is cut from the larger piece of fabric which is formed, for example, by braiding wire strands to form a long tubular braid. When cutting the fabric to the desired dimensions, care should be taken to ensure that the fabric will not unravel. One may solder, braze, weld, coat, glue, clamp, tie or otherwise affix the ends of the desired length together. According to one embodiment, each layer of the device may comprise 36-144 wire strands ranging in diameter from about 0.001 to 0.006 in. formed of a shape memory alloy, such as Nitinol, that are braided so as to define fenestrations with an area of about 0.00015 to 0.015 sq. in., which are sufficiently small so as to slow the blood flow through the wall of the device and to facilitate thrombus formation thereon. Inner and outer braided layers may have pitch angles that are about equal to obtain desirable collapse and expansion characteristics, such as maintaining a uniform overall length.

Once an appropriately sized piece of the metal fabric is obtained, the fabric is deformed to generally conform to a surface of a molding element. Deforming the fabric will reorient the relative positions of the wire strands of the metal fabric from their initial order to a second, reoriented configuration. The shape of the molding element may be selected to deform the fabric into substantially the shape of the desired medical device when unconstrained. Once the molding element is assembled with the metal fabric generally conforming to a molding surface of that element, the fabric may be subjected to a heat treatment while it remains in contact with that molding surface. After the heat treatment, the fabric is removed from contact with the molding element and will substantially retain its shape in a deformed state. As explained in further detail below in conjunction with the illustrated embodiments, different configurations of devices may be formed and heat set for various locations within the body.

Those skilled in the art will appreciate that in order to speed up the occlusion of the vessel, the device may be coated with a suitable thrombogenic agent, filled with a polyester fiber, or braided with an increased number of wire strands. The interwoven fiber may attach to a clot to retain the clot firmly within the device as it forms the occlusion.

The device may include a plurality of planes of occlusion. A plane of occlusion may be any surface, whether flat or irregular in shape, that may be oriented at least partially transverse to the flow of blood so as to facilitate the formation of thrombus. At least one plane of occlusion may include one or more layers of occlusive material, such as a layer of fabric and/or a layer of polyester fiber, two layers of metal, or two layers of polyester. Thus, by modifying the configuration of the device, the number of planes of occlusion may be modified, and by changing the number of layers of occlusive material, the rate at which the device occludes the vascular abnormality may also be modified.

Once a device having a preselected shape has been formed, the device may be used to treat a physiological condition of a patient. A medical device suitable for treating the condition, which may be substantially in accordance with one of the embodiments outlined below, is selected. Once the appropriate medical device is selected, a catheter or other suitable delivery device may be positioned within a channel in a patient's body to place the distal end of the delivery device adjacent the desired treatment site, such as immediately adjacent (or even within) the shunt of an abnormal opening in the patient's organ for example.

In one embodiment, the device does not have end clamps and the delivery device engages the wire ends at the proximal end of the device between a sleeve and a bead. The sleeve may be connected to a hollow shaft, and the bead may be connected to a cable or wire that passes through the shaft. Relative movement between the bead and the sleeve either engages or releases the braid wire ends at the proximal end of the device. When the wire ends are engaged the delivery device can control the advancement of the device through the delivery catheter. For a further exemplary discussion regarding this delivery device as well as an over the wire version of it, see U.S. Patent Appl. Publ. No. 2007/0118207 to Amplatz et. al., which is hereby incorporated in its entirety by reference.

The delivery device (not shown) can take any suitable shape, such as an elongate flexible metal shaft or hypotube or metal braided polymer tube configured to constrain the medical device. The delivery device can be used to urge the medical device through the lumen of a catheter/sheath for deployment in a channel of a patient's body. When the medical device is deployed out the distal end of the catheter, the delivery device still will retain it. As also explained in further detail below, the specific delivery method will depend on the particular device to be deployed within the body.

In one embodiment the medical device, the delivery device and the delivery catheter/sheath accommodate a coaxial guidewire that slideably passes through the medical device), delivery device and delivery catheter/sheath central lumen, and therefore helps guide the delivery device and delivery catheter/sheath to the desired location. The guidewire may be delivered independently through the vasculature and across the targeted treatment location or may be extended partially distal to the distal end of the delivery device and catheter/sheath, and advanced with the delivery device and catheter/sheath while the guidewire is manipulated to guide the medical device to the desired location. In another embodiment, the catheter/sheath is steerable to assist in placement of the delivery device. For further discussion regarding a delivery device and methods that may be used to deploy a device according to various aspects of the present invention, see U.S. patent application Ser. No. 11/966,397, which is hereby incorporated in its entirety by reference.

By keeping the medical device attached to the delivery device, the operator can retract the device for repositioning relative to the abnormal opening, if it is determined that the device is not properly positioned. A delivery device attached to the medical device may allow the operator to control the manner in which the medical device is deployed out the distal end of the catheter. When the medical device exits the catheter, it will tend to resiliently return to a preset, expanded shape, which is set when the fabric is heat-treated. When the device self expands and springs back into this shape, it may tend to act against the distal end of the catheter effectively urging itself forward beyond the end of the catheter. This spring action could conceivably result in improper positioning of the device if the location of the device within the body is critical, such as where it is being positioned in a shunt between two vessels. Since the delivery device can enable the operator to maintain a hold on the device during deployment, the spring action of the device can be controlled by the operator to ensure proper positioning during deployment.

The medical device can be constrained into its reduced diameter configuration and inserted into the lumen of the catheter. For instance, the medical device may be reduced to an outer diameter capable of being delivered within a catheter having an inner diameter of about 11 French or less. The collapsed configuration of the device may be of any shape suitable for easy passage through the lumen of a catheter and proper deployment out the distal end of the catheter. For example, the device may have a relatively elongated collapsed configuration wherein the device is stretched along its axis. This collapsed configuration can be achieved simply by stretching the device generally along its axis, e.g. by manually grasping the ends of the device and pulling them apart, which will tend to collapse the expanded diameter portions of the device inwardly toward the device's axis. In this regard, these devices are not unlike "Chinese handcuffs", which tend to constrict in diameter under axial tension.

If the device is to be used to permanently exclude a channel in the patient's body, one can simply retract the catheter and remove it from the patient's body. This will leave the medical device deployed in the patient's vascular system so that it may exclude the target site, such as an aneurysm or other channel in the patient's body. In some circumstances, the medical device may be attached to a delivery system in such a manner as to secure the device to the end of the delivery device. Before removing the catheter in such a system, it may be necessary to detach the medical device from the delivery device before removing the catheter and the delivery device.

Although the device will tend to resiliently return to its initial expanded configuration, i.e., its shape prior to being collapsed for passage through the catheter, it should be understood that it might not always return entirely to that shape. For example, it may be desirable that the device has a maximum outer diameter in its expanded configuration at least as large as and preferably larger than, the inner diameter of the opening in which it is to be deployed. For instance, the outer diameter of the device may be about 10-30% larger than the inner diameter of the opening. If such a device is deployed in a vessel or abnormal opening having a small lumen, engagement with the lumen will prevent the device from completely returning to its expanded configuration. Nonetheless, the device would be properly deployed because it would engage the inner wall of the lumen to seat and retain the device therein.

When the device is deployed in a patient, thrombi will tend to collect on the surface of the strands. By having a greater strand density and smaller flow passages between strands as afforded by the multiple layer construction of the present invention, the total surface area of the strands and flow resistance will be increased, increasing the thrombotic activity of the device and permitting it to relatively rapidly restrict or shunt flow through the vessel in which it is deployed or in the case of a graft, occlude the wall of the stent graft to exclude an aneurysm, but not occlude the vessel.

The device may be delivered and properly placed using two dimensional ICE, MRI, transesophageal echocardiograpy, angiography, and/or Doppler color flow mapping. With the advent of two dimensional ICE, MRI, trans-esophageal echocardiography, bi-plane angiography, and Doppler color flow mapping, the approximate anatomy of the defect can be visualized. The device that is employed will be based on the approximate size of the vessel or abnormality in which the device is to be placed.

Figure 1:
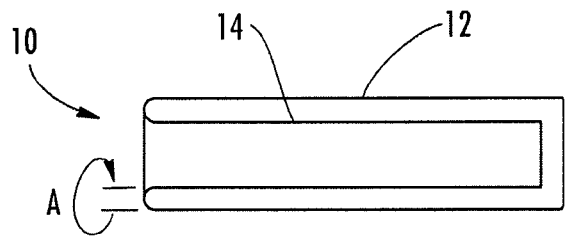
Figure 2:
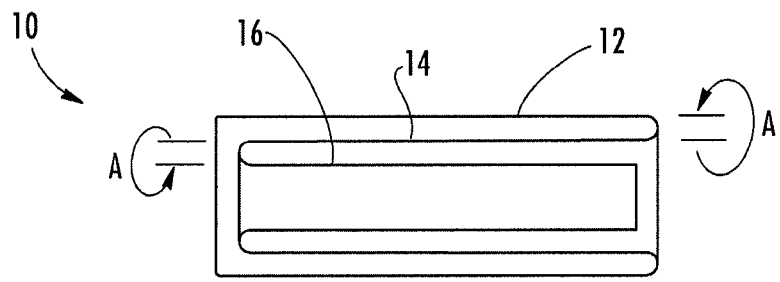
Figure 3:
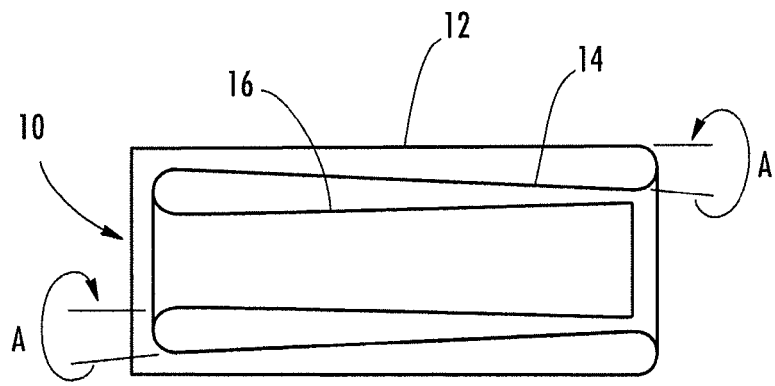

Referring now to the drawings, a discussion of the embodiments of various medical devices of the present invention will next be presented. FIG. 1 illustrates a first embodiment of a medical device 10 for treating a target site. For example, the medical device 10 could be a stent graft used for treating various body lumens, such as for treating an aneurysm. As briefly mentioned above, the medical device 10 is heat set to include an overlapping configuration, as shown in FIG. 1. In particular, the medical device 10 includes a pair of overlapping layers 12, 14 that define a cylindrical structure having an overlapping configuration. In particular, the pair of layers 12, 14 are formed by inverting a single layer of occlusive material within itself in an axial direction. For example, one layer 14 may be folded inward within an outer layer 12. When fully deployed and unconstrained, at least a portion of each overlapping layer 12, 14 may be configured to lie adjacent to one another. Each layer 12, 14 is configured to overlap one another substantially along its entire length. Thus, the occlusive material of the medical device 10 may be folded approximately midway along its longitudinal axis to form the layers 12, 14. FIGS. 2 and 3 depict an additional embodiment where the medical device 10 includes three overlapping layers 12, 14, 16. Thus, the occlusive material may be folded twice to form the overlapping layers 12, 14, 16, wherein each layer is approximately the same length.

Moreover, the occlusive material may have a different pick count along its length such that portions of the material having different pick counts may correspond to different layers. For instance, the layers 12, 14, 16 may have the same or a different pick count from one another. As such, problems that may occur with the symmetry of elongation and dissimilar braid geometries of multi-layered medical devices may be reduced by a medical device that may be elongated and delivered as a single layer and subsequently deployed as a multi-layered device.

Thus, the medical device 10 may include any number of overlapping layers. In addition, the overlapping layers 12, 14, 16 may be inverted at various angles with respect to one another. For instance, FIG. 1 shows that the layer 14 is inverted within layer 12 by an angle "A" of 180° or less. Similarly, FIG. 2) shows that the layers 12, 14, 16 have been inverted 180° or less with respect to one another. In an alternative aspect, FIGS. 3 and 4 demonstrate that the layers 12, 14, 16 may be inverted greater than 180° with respect to one another. Thus, at least one of the layers 12, 14, 16 may be non-parallel with respect to a longitudinal axis of the medical device 10, while one or more other layers may be parallel to a longitudinal axis of the medical device. As such, at least a portion of the overlapping layers 12, 14, 16 may not lie adjacent to one another.

Figure 4:
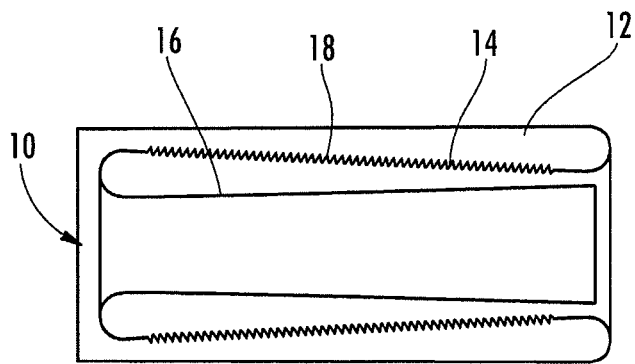

Moreover, FIG. 4 demonstrates that the medical device 10 may further include one or more layers of polyester fabric 18 positioned between respective overlapping layers 12, 14, such as layers of metallic fabric. According to one embodiment, the polyester fabric layer 18 may be attached to the metallic fabric layers 12 or 14 or woven in with the metal fabric layers over a selected portion after heat treatment of the metallic fabric. In addition, a portion of the metal fabric surface of the layers 12, 14, 16, such as layer 14 in FIGS. 2-4, may also be formed with a ribbed, corrugated, or pleated surface portion to increase radial strength of the medical device 10 and/or to provide spacing between layers to improve thrombus formation or facilitate tissue in growth.

FIG. 5A illustrates a medical device 10 in an elongated, non-overlapping configuration. That is, the overlapping layers 12, 14, 16 of the medical device 10 may be separated from one another into a non-overlapping configuration for delivery within a catheter, as explained in further detail below. The non-overlapping configuration may have different diameters in different locations and a greater length than the overlapping configuration. Accordingly, because the medical device 10 may be delivered in a non-overlapping configuration, the medical device may be delivered within a catheter having a smaller diameter than other multi-layered medical devices that are not capable of being separated. Moreover, the medical device 10 may include raised or recessed surfaces or similar irregularities 20, 22, which may correspond to heat set, inversion points. These surface irregularities 20, 22 may be felt during delivery of the device as they pass through the delivery catheter tip and may serve as a means of tactile feedback to alert the operator of the stage of device delivery even without visualization by other means. Various techniques could be employed to fabricate the medical device 10. According to one embodiment and with reference to FIG. 5A, a medical device 10 is formed from a single layer of occlusive material. For instance, the medical device 10 may be braided to form a tubular fabric made of an elastic metallic material such as Nitinol. The medical device 10 may be inverted to form a plurality of overlapping layers and then heat set in a mold or by placing a mandrel in the inside to maintain the desired inside shape. For example, one end of the medical device 10 may be pushed distally inside itself to form the overlapping layers 12, 14, 16. When the desired overlapping configuration is obtained, the medical device 10 would then be heated in a mold to a predetermined temperature and for a length of time sufficient to heat set the overlapping layers 12, 14, 16. Thus, when the medical device 10 is forced from the overlapping configuration to the non-overlapping configuration, such as by elongating the medical device, the layers do not return to the overlapping configuration when the force is removed but instead take on the relaxed shape as shown in FIG. 5B. During delivery and after the first layer 12 is deployed, a force may be applied to the fabric, by advancement of the delivery device in the distal direction, to cause the first inversion to occur. Once the first layer 12 has been inverted, the fabric will have the propensity to return to its heat set configuration and expel itself from the delivery catheter so as to form the middle layer 14. Continued advancement of the fabric from the delivery catheter will deliver the third layer 16, which results in the overlapping configuration shown in FIG. 5C.

In use, the medical device 10 would be delivered at a diameter that is smaller than its heat set diameter such as shown in FIG. 5A. Typically, the medical device 10 would be constrained, such as by axially elongating the medical device to a smaller diameter and positioning the distal end of the fabric wires within a delivery catheter for delivery to a target site. A funnel shaped introducer device may be employed to facilitate the insertion of the device by having the distal end of the funnel inserted into the delivery catheter proximal end lumen and advancing the braid into the lumen. Alternatively the delivery device may be inserted through the delivery catheter lumen, exiting the distal end of the catheter and attached to the proximal end of the device end connector or fabric end, and the device pulled proximally into the delivery catheter lumen. In either case the delivery device may be releasably attached to the medical device 10 prior to insertion into the delivery catheter. The delivery catheter, medical device, and delivery device, would be introduced into the patient together, through an introducer sheath and placed using the Seldinger technique to gain vascular access such as through the femoral artery. The medical device would then be guided through the vascular system until a distal end of the delivery catheter is proximate to a target site to be treated, such as within a lumen. With the medical device 10 and the delivery device held stationary, the delivery catheter is withdrawn in the proximal direction to partially eject the medical device from the distal end of the delivery catheter until a distal portion or layer 12 of the medical device then self-expands to engage the lumen. The natural tendency of the medical device 10 is to return to the expanded heat set configuration, once released from the catheter, although some intervention by the physician may be necessary in order for the medical device to return to the overlapping heat set configuration and be fully deployed. To fully deploy the layer 12 the physician may need to further retract the delivery catheter while advancing the delivery device until either visual or tactile feedback indicates the first layer is fully deployed. Once the layer 12 of the medical device 10 is deployed, the physician may then urge the delivery device and or delivery catheter distally so as to force the medical device to invert within itself to initially begin the formation of layer 14. Distal advancement of the delivery device and/or proximal retraction of the delivery catheter may result in deploying layer 14 as the layer returns to its inverted heat set configuration. To fully deploy the device 10, the delivery catheter may be withdrawn proximally to the proximal end of overlapping layers 12 and 14. While holding the delivery catheter stationary and distally advancing the delivery device the layer 16 will be formed. When the medical device 10 is fully deployed from the delivery catheter, the clamp member may be actuated to release the proximal end of the medical device 10 and allow the proximal end of layer 16 to self expand. According to one embodiment, the medical device 10 may be positioned within a lumen to bridge or exclude an aneurysm, with the medical device engaging the lumen upstream and downstream of the aneurysm. For further exemplary details regarding a delivery catheter, a delivery device, clamp member, and over-the-wire delivery, and methods of using the same, Applicants hereby incorporate U.S. Patent Appl. Publ. No. 2006/0253184, filed May 4, 2005 and U.S. Patent Appl. Publ. No. 2007/0118207A1, filed Jan. 17, 2007, herein in their entirety.

In an alternative technique for delivering a medical device, a guide wire may be inserted through an introducer sheath and advanced to the treatment site. A delivery catheter may then be introduced over the guide wire and tracked to the treatment site. The medical device attached proximally to the delivery device may then be introduced over the guide wire or alternatively the guide wire removed. The distal end of the device may be loaded into the funnel introducer and fed into the proximal lumen of the delivery catheter and advanced using the delivery device to place the distal end of the device near the distal end of the delivery catheter. The medical device may then be deployed as previously described above.

FIG. 6A illustrates an embodiment of a medical device 200 that may be employed as a flow restrictor or a shunt. The medical device 200 includes an overlapping configuration having three overlapping layers 202, 204, 206. As described above, the outer layer 202 and middle layer 104 are inverted greater than 180° with respect to one another, while the middle layer 204 and inner layer 206 are also inverted greater than 180°. Thus, while the proximal 208 and distal 210 ends have openings for allowing fluid to flow therethrough, a diameter of at least a portion of the passageway extending through the medical device 200 is smaller than the diameter of the body lumen 212. The fabric surfaces facilitate the formation of thrombus and, in effect, block flow through all but the central passageway. Thus, the medical device 200 is configured to restrict the amount of fluid flowing between the proximal 208 and distal 210 ends. The medical device 200 may be configured such that the proximal end 208 has a larger opening than the distal end 210. Or, a plurality of the layers 202, 204, 206 may be configured to fold at particular regions, such as along the entire length of the medical device 200 as shown in FIG. 6A, at a medial portion as shown in FIG. 6B, and at the distal end 210 as shown in FIG. 6C. Thus, the location and number of the overlapping layers 202, 204, 206 may be varied to achieve a desired configuration of a flow restrictor in a particular body lumen. Moreover, FIGS. 6B and 6C show that the proximal 208 and/or distal 210 ends may have a flared end with no overlapping layers that have a larger lumen diameter than the portion of the medical device 200 corresponding to the overlapping layers.

According to another embodiment, a medical device 300 is shown in FIG. 7, which may be employed as a shunt for restricting flow through a septum 302. The medical device 300 includes a plurality of overlapping layers 304, 306, 308 that overlap at the proximal 310 and distal 312 ends of the medical device. Each layer 304, 306, 308 extends obliquely with respect to an axis extending through the lumen of the medical device 300. The layers 304, 306, and 308 act together to apply force against the septum 302 on each side to maintain the device in place. In addition, the proximal 310 and distal 312 ends may be funnel shaped and have a larger lumen diameter than the non-overlapping portion of the medical device 300 extending therebetween. The outer layer 304 is configured to conform to the septum 302. As described above, the proximal 310 and distal 312 ends of the medical device 300 may be displaced away from one another to separate the overlapping layers 304, 306, 308 for delivery as a single layer within a catheter.

As described above, the specific technique used to deliver a medical device may vary based on the type of medical device and where the device is being deployed. For example, FIGS. 1-7 show no end clamps, wherein the proximal end of the medical devices may be engaged by a delivery device having a locking member configured to lock onto the proximal end circumference of the medical device. Thus, grasping one free end of the medical device and the locking member of the delivery device may be used to engage the proximal and distal ends and pull the ends of the medical device apart so as to separate the overlapping layers of material into a single layer of material for delivery within a catheter. Although the medical device embodiments shown in FIGS. 1-7, may be configured to spring back to the expanded heat set configuration when deployed from the delivery catheter, further user intervention, may be necessary in some instances in order to facilitate folding of the material into overlapping layers. This may be particularly true at the point of inversion from outer layer to first inverted inner layer where the fabric is somewhat resistant due to an over-center condition in which the outer diameter of the outside layer proximal end must be expanded a small amount to allow for the inversion to occur.

Embodiments of the present invention may provide several advantages. For example, a medical device having a plurality of overlapping layers may be separated into a single layer for delivery within a catheter. Thus, the medical device may be delivered within a catheter having a smaller inner diameter than multi-layered medical devices that may not otherwise be capable of being separated into a single layer. Therefore, the medical device may provide the benefits of a multi-layered device after deployment while providing the benefits of a single-layered device prior to deployment. As such, the device may be capable of being delivered to more difficult to access locations within the body, as well as be delivered through smaller diameter vessels, openings, cavities, and the like. Moreover, the medical device may be used to exclude, shunt, restrict flow, or reline vessels, lumens, cavities, aneurysms, or organs anywhere in the vasculature or body.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, thy are used in a generic and descriptive sense only and not for purposes of limitation.

That which is claimed:

1. A medical device comprising:
a tubular occlusive material having a proximal end and a distal end and a continuous layer of braided fabric extending entirely therebetween in a non-overlapping configuration, the occlusive material further comprising a preset, overlapping configuration comprising at least three overlapping layers folded over by inversion with respect to one another and defining a proximal end and a distal end, the at least three overlapping layers comprising an outer layer and a plurality of inner layers, the outer layer extending from the proximal end of the occlusive material in the overlapping configuration to the distal end of the occlusive material in the overlapping configuration and the plurality of inner layers being contained between the proximal end and the distal end of the occlusive material in the overlapping configuration, wherein the at least three overlapping layers are configured to be separated and disposed within a catheter in the non-overlapping configuration and are biased to return to the preset, overlapping configuration when deployed from the catheter, wherein the occlusive material is configured to provide a central passageway for fluid flow therethrough in the preset, overlapping configuration, and wherein the occlusive material in the non-overlapping configuration comprises a different pick count along a length thereof such that, in the overlapping configuration, at least one of the overlapping layers comprises a different pick count than at least one other of the overlapping layers.

2. The medical device of claim 1, wherein the fabric comprises braided strands of a shape memory alloy.

3. The medical device of claim 1, wherein the occlusive material is configured to be axially elongated to separate the at least three overlapping layers into the non-overlapping configuration prior to deploying the occlusive material.

4. The medical device of claim 1, wherein the occlusive material comprises an overlapping configuration defining a tubular member, and wherein the tubular member includes a side wall defined by the at least three overlapping layers.

5. The medical device of claim 4, wherein the outer diameter of the tubular member is at least about 1 cm, and a thickness of the sidewall is about 3 mm or less.

6. The medical device of claim 1, wherein each layer of the at least three layers of occlusive material comprises approximately the same length.

7. The medical device of claim 1, wherein the occlusive material comprises an inner surface and an outer surface, and wherein at least a portion of the occlusive material is configured to fold within itself such that a portion of the inner surface overlies another portion of the inner surface.

8. The medical device of claim 1, wherein the occlusive material comprises an inner surface and an outer surface, and wherein at least a portion of the occlusive material is configured to fold within itself such that a portion of the outer surface overlies a portion of the inner surface.

9. The medical device of claim 1, wherein at least a portion of at least one of the at least three overlapping layers is configured to fold within and lie adjacent to another layer.

10. The medical device of claim 1, wherein at least one pair of the at least three overlapping layers are configured to fold greater than 180 degrees with respect to one another.

11. The medical device of claim 10, wherein at least a pair of non-adjacent overlapping layers include surface portions that are configured to lie substantially parallel to one another in the overlapping configuration.

12. The medical device of claim 1, wherein at least one pair of the at least three overlapping layers are configured to fold greater than about 135 degrees with respect to one another.

13. The medical device of claim 1, wherein the occlusive material is configured to be constrained to an outer diameter of less than about 11 French for delivery within a catheter in the non-overlapping configuration.

14. The medical device of claim 1, wherein the overlapping configuration has a larger outer diameter and a shorter length than the non-overlapping configuration.

15. The medical device of claim 1, wherein the occlusive material is configured to be one of a stent graft, a shunt, or a flow restrictor device.

16. The medical device of claim 1, wherein the preset, overlapping configuration comprises an expanded heat-set configuration such that the occlusive material is configured to self expand from the non-overlapping configuration and return to the preset, overlapping configuration when deployed from a catheter.

17. The medical device of claim 1, wherein at least two of the layers extend from one of the proximal or distal ends of the occlusive material in the overlapping configuration and toward the other end.

18. A medical device comprising:
a tubular occlusive material having a preset, overlapping configuration comprising a plurality of at least three overlapping layers and defining a proximal end and a distal end, the at least three overlapping layers comprising an outer layer and a plurality of inner layers, the outer layer extending from the proximal end to the distal end and the plurality of inner layers being contained between the proximal end and the distal end, wherein an adjacent pair of the overlapping layers are folded by inverting greater than 180 degrees with respect to one another such that the adjacent pair of overlapping layers extend along respective longitudinal axes that are non-parallel to one another, wherein the at least three overlapping layers are configured to be separated and disposed within a catheter in a non-overlapping configuration and are configured to return to the preset, overlapping configuration when deployed from the catheter, and wherein the occlusive material in the non-overlapping configuration comprises a different pick count along a length thereof such that, in the overlapping configuration, at least one of the overlapping layers comprises a different pick count than at least one other of the overlapping layers.

19. The medical device of claim 18, wherein at least a pair of non-adjacent overlapping layers include surface portions that are configured to be substantially parallel to one another in the overlapping configuration.

20. A medical device comprising:
an occlusive material defining a tubular member having a preset, overlapping configuration, the preset, overlapping configuration comprising at least three overlapping layers folded over one another and defining a proximal end and a distal end, the at least three overlapping layers comprising an outer layer and a plurality of inner layers, the outer layer extending from the proximal end to the distal end and the plurality of inner layers being contained between the proximal end and the distal end, wherein the at least three overlapping layers are configured to be separated and disposed within a catheter in a non-overlapping configuration and are configured to return to the preset, overlapping configuration, wherein the occlusive material is configured to provide a central passageway for fluid flow therethrough in the preset, overlapping configuration, and wherein the occlusive material in the non-overlapping configuration comprises a different pick count along a length thereof such that, in the overlapping configuration, at least one of the overlapping layers comprises a different pick count than at least one other of the overlapping layers.

21. The medical device of claim 20, wherein at least one overlapping layer overlaps at least 50% of another overlapping layer.

22. The medical device of claim 21, wherein the at least one overlapping layer substantially coextends within another layer.

* * * * *